(12) United States Patent
Groeger et al.

(10) Patent No.: US 7,824,899 B2
(45) Date of Patent: Nov. 2, 2010

(54) PREPARATION OF ENANTIOMERICALLY ENRICHED AMINES AND AMIDES BY ENZYMATIC RESOLUTION USING A SULFONYLACETIC ACID ESTER AS ACYL DONOR

(75) Inventors: Harald Groeger, Hanau (DE); Oliver May, Aachen (DE); Kai Rossen, Hanau (DE); Karlheinz Drauz, Freigericht (DE)

(73) Assignee: Evonik Degussa GmbH, Essen (DE)

( * ) Notice: Subject to any disclaimer, the term of this patent is extended or adjusted under 35 U.S.C. 154(b) by 726 days.

(21) Appl. No.: 11/766,164

(22) Filed: Jun. 21, 2007

(65) Prior Publication Data

US 2007/0298471 A1    Dec. 27, 2007

(30) Foreign Application Priority Data

Jun. 21, 2006    (DE) .................. 10 2006 028 818

(51) Int. Cl.
*C12P 41/00*    (2006.01)
(52) U.S. Cl. ...................................... 435/280
(58) Field of Classification Search .................. None
See application file for complete search history.

(56) References Cited

U.S. PATENT DOCUMENTS

| 6,869,781 | B2 | 3/2005 | Groger et al. |
|---|---|---|---|
| 6,897,010 | B2 | 1/2006 | Groger et al. |
| 6,987,010 | B2 | 1/2006 | Groger et al. |
| 2006/0216801 | A1 | 9/2006 | Groger et al. |
| 2006/0246561 | A1 | 11/2006 | Hummel et al. |
| 2007/0020741 | A1 | 1/2007 | Drauz et al. |

| 2007/0149781 | A1 | 6/2007 | Riermeier et al. |
|---|---|---|---|
| 2009/0117627 | A1 | 5/2009 | Doderer et al. |

FOREIGN PATENT DOCUMENTS

| WO | WO 97/20946 | 6/1997 |
|---|---|---|
| WO | WO 97/41214 | 11/1997 |

OTHER PUBLICATIONS

Itoh et al., "Enhanced enantioselectivity of an Enzymatic Reaction by the Sulfur functional Group. A Simple Preparation of Optically Active beta-Hydroxy Nitriles Using a Lipase", J. Organic Chemistry 56 : 1521-1524 (1991).*
U.S. Appl. No. 11/629,407, filed Dec. 13, 2006, Groeger, et al.
U.S. Appl. No. 11/766,189, filed Jun. 21, 2007, Groeger, et al.
U.S. Appl. No. 10/593,119, filed Mar. 10, 2005, Schulze, et al.

* cited by examiner

*Primary Examiner*—Sandra Saucier
(74) *Attorney, Agent, or Firm*—Oblon, Spivak, McClelland, Maier & Neustadt, L.L.P.

(57) ABSTRACT

A process for the preparation of an enantiomerically enriched amine, is performed by a) cleaving a racemic mixture of a reaction product of i) a chiral amine and ii) an acyl donor, in the presence of a hydrolase, to obtain a mixture of an enantiomerically enriched amide and an enantiomerically enriched amine; or b) reacting an amine with an acyl donor, in the presence of a hydrolase, to obtain a mixture of an enantiomerically enriched amide and an enantiomerically enriched amine; and c) separating the enantiomerically enriched amide from the enantiomerically enriched amine, wherein the acyl donor is a sulphonylacetic acid ester. The process (1) leads to high enantioselectivities, and (2) high reactivities, (3) is based on an acyl donor accessible in a simple manner, (4) is suitable for a large number of very different substrates and/or (5) is suitable for carrying out at high substrate concentrations.

15 Claims, No Drawings

PREPARATION OF ENANTIOMERICALLY ENRICHED AMINES AND AMIDES BY ENZYMATIC RESOLUTION USING A SULFONYLACETIC ACID ESTER AS ACYL DONOR

BACKGROUND OF THE INVENTION

1. Field of the Invention

The present invention relates to a process for the resolution of amines by reaction with an ester as an acyl donor in the presence of a hydrolase and subsequent separation of the enantiomerically enriched amide from the unreacted, enantiomerically enriched amine.

2. Description of the Related Art

The resolution of amines by enzyme-catalyzed reaction with esters is known in various embodiments in the literature. In an early study, the resolution of amines using trifluoroethyl butyrate as the acyl donor and subtilisin as the enzyme component is already described in 1989 (H. Kitaguchi, P. A. Fitzpatrick, J. E. Huber, A. M. Klibanov, J. Am. Chem. Soc. 1989, 111, 3094). However, selectivities varying in a wide range were obtained. The reaction times were also in a range which is unsatisfactory for industrial applications.

A large number of studies are based on the use of alkyl acetates, for example using ethyl acetate and butyl acetate. In a first general synthesis, for this purpose high enantiomeric excesses of 90-98% ee for the amide formed were obtained using ethyl acetate as the acyl donor and a lipase from *Candida antarctica* (M. T. Reetz, C. Dreisbach, Chimia 1994, 48, 570). However, the conversions were in a wide range from 20-44%, although large amounts of enzyme were used as a catalyst. The reaction times were also in a wide range from 7 to 60 hours.

A detailed investigation of this method confirmed the long reaction times, which when using ethyl acetate as the acyl donor and a lipase from *C. antarctica* were between 5 and 21 days (B. A. Davis, D. A. Durden, Synth. Commun. 2001, 31, 569). Acyl donors having prolonged chain lengths were likewise employed, but when using ethyl decanoate as the acyl donor and a lipase from *C. antarctica* only led to a low conversion (A. Goswami, Z. Guo, W. L. Parker, R. N. Patel, Tetrahedron: Asymmetry 2005, 16, 1715).

The use of ethyl methoxyacetate as an acyl donor in the enzymatic resolution of amines using a lipase from *Burkholderia plantarii* led to a high reaction rate, the use of MTBE as the preferred solvent being emphasized (F. Balkenhohl, K. Ditrich, B. Hauer, W. Ladner, J. Prakt. Chem. 1997, 339, 381; Review: M. Breuer, K. Ditrich, T. Habicher, B. Hauer, M. Keβeler, R. Stürmer, T. Zelinski, Angew. Chem. 2004, 116, 806). However, large amounts of enzyme of >10 000 000 units per mole of substrate are also employed. The resolution using ethyl methoxyacetate likewise proceeds successfully when using a lipase from *Candida antarctica* as a biocatalyst (U. Steltzer, C. Dreisbach, DE Pat. 19637336, 1996).

Further enzymatic resolution methods are based on the use of dialkyl, diallyl and divinyl carbonates (C.-H. Wong, B. Orsat, W. J. Moree, S. Takayama, U.S. Pat. No. 5,981,267, 1999; B. Orsat, P. B. Alper, W. Moree, C.-P. Mak, C.-H. Wong, J. Am. Chem. Soc. 1996, 118, 712). Using phenylallyl carbonate, an "unsymmetrically substituted" carbonate was additionally also found to be a suitable acyl donor for the lipase-catalyzed resolution of amines (G. F. Breen, Tetrahedron: Asymmetry 2004, 15, 1427). However, the unsatisfactory enantioselectivities often obtained are disadvantageous.

Moreover, ethyl acrylates were also employed as esters in the enzymatic resolution of aliphatic amines, high enantiomeric excesses of up to 95% ee being obtained for the remaining amine (S. Puertas, R. Brieva, F. Rebolledo, V. Gotor, Tetrahedron 1993, 49, 4007). However, the reaction times were a long 7 to 11 days, which is not appealing for industrial use.

A further acyl donor employed is cyanomethyl pent-4-enoate, cost-effective access to this acyl donor being problematical (S. Takayama, W. J. Moree, C.-H. Wong, Tetrahedron Lett. 1996, 37, 6287).

In EP 865500, the enzymatic resolution of amides is mentioned, compounds of the general formula 1 being reacted in the presence of the lipase from *Candida antarctica*.

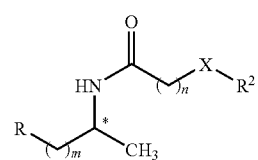

1

X here can be both oxygen and sulphur. Only examples for X=O are shown.

SUMMARY OF THE INVENTION

It is an object of the present invention to provide a process for the preparation of enantiomerically enriched amines, which (1) leads to high enantioselectivities, and (2) high reactivities, (3) is based on an acyl donor accessible in a simple manner, (4) is suitable for a large number of very different substrates and/or (5) is suitable for carrying out at high substrate concentrations. Against the background of economical and ecological process management, a process of this type is particularly suitable.

This and other objects have been achieved by the present invention the first embodiment of which includes a process for the preparation of an enantiomerically enriched amine, comprising:

a) cleaving a racemic mixture of a reaction product of i) a chiral amine and ii) an acyl donor, in the presence of a hydrolase, to obtain a mixture of an enantiomerically enriched amide and an enantiomerically enriched amine; or b) reacting an amine with an acyl donor, in the presence of a hydrolase, to obtain a mixture of an enantiomerically enriched amide and an enantiomerically enriched amine; and c) separating the enantiomerically enriched amide from the enantiomerically enriched amine, wherein said acyl donor is a sulphonylacetic acid ester of the formula 2

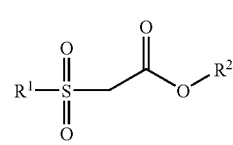

2 wherein $R^1$ and $R^2$ independently of one another are $(C_1\text{-}C_8)$-alkyl, HO—$(C_1\text{-}C_8)$-alkyl, $(C_2\text{-}C_8)$-alkoxyalkyl, $(C_6\text{-}C_{18})$-aryl, $(C_7\text{-}C_{19})$-aralkyl, $(C_3\text{-}C_{18})$-heteroaryl, $(C_4\text{-}C_{19})$-heteroaralkyl, $(C_1\text{-}C_8)$-alkyl-$(C_6\text{-}C_{18})$-aryl, $(C_1\text{-}C_8)$-alkyl-$(C_3\text{-}$ $C_{18}$)-heteroaryl, ($C_3$-$C_8$)-cyclo-alkyl, ($C_1$-$C_8$)-alkyl-($C_3$-$C_8$)-cycloalkyl, or ($C_3$-$C_8$)-cycloalkyl-($C_1$-$C_8$)-alkyl.

DETAILED DESCRIPTION OF THE INVENTION

An object of the present invention is achieved, extremely surprisingly, but for that no less advantageously, by a process for the preparation of enantiomerically enriched amines by a) cleavage of a racemic mixture of a reaction product of a chiral amine and an acyl donor or b) reaction of a chiral amine with an acyl donor in the presence of a hydrolase and subsequent separation of the enantiomerically enriched amide from the enantiomerically enriched amine, in such a way that the acyl donor used is a sulphonylacetic acid ester of the formula 2

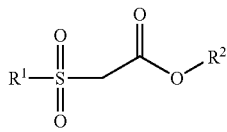

2 in which $R^1$ and $R^2$ independently of one another are ($C_1$-$C_8$)-alkyl, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, or ($C_3$-$C_8$)-cycloalkyl-($C_1$-$C_8$)-alkyl.

As a rule, the products are obtained in very good space/time yields and with high enantiomeric excesses. The compounds of the formula 2 can be easily prepared and can also optionally be used a number of times after recycling, like the enzyme, which helps to cut the substance use costs even further.

In the context of the present invention, a there is no particular limitation on the choice of the compounds of the formula 2. Preferably, compounds of formula 2 are used which have adequate reactivity, are easily obtained and have as low as possible production costs. Compounds are therefore preferred in which $R^1$ and $R^2$ are an alkyl or aryl radical. $R^1$ is preferably an alkyl, in particular methyl, or aryl radical, in particular p-tolyl, and $R^2$ as an alkyl, benzyl or aryl radical. Very particularly preferably, p-tolyl- or methylsulphonylacetate is used as the ester.

Chiral amines according to the present invention are all amines known to the artisan having at least one center, plane or axis of chirality. Preferred amines are those having a center of chirality in a 1-, or 2-position remote from the nitrogen atom. Preferred amines embracing chiral planes are those having a ferrocenyl moiety attached in the 1- or 2-position counted from the nitrogen atom. In a further preferred way the amines of the invention are those of the following formula $R^3$—NH—$R^4$ wherein $R^3$, $R^4$ are independently of each other ($C_1$-$C_8$)-alkyl, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, or ($C_3$-$C_8$)-cycloalkyl-($C_1$-$C_8$)-alkyl or in which $R^3$ and $R^4$ build up a ring structure. In addition $R^4$ can be H, too.

There is no particular limitation on the hydrolase to be used in the present invention. Hydrolases such as those described in the literature may be used (for a survey, see, for example: U. Bornscheuer, R. J. Kazlauskas, Hydrolases in Organic Synthesis, 2nd Edition, Wiley-VCH-Verlag, Weinheim, 2005). Preferably, lipases from *Candida antarctica, Burkholderia plantarii* and *Mucor miehei* are used. Very particularly preferably, a lipase from *Candida antarctica*, preferably in immobilized form (e.g. Novozym 435), is used as the enzyme component. There is no particular limitation on the type and manner of immobilization of the lipases and hydrolases. For a summary of the immobilization of enzymes, see J. Lalonde in: Enzyme Catalysis in Organic Synthesis (ed.: K. Drauz, H. Waldmann), Volume 1, 2nd Edition, Wiley-VCH-Verlag, Weinheim, pp. 163-184.

There is no particular limitation on the reaction temperature. Preferably, the reaction temperature is chosen so that a reaction rate is achieved which is as high as possible combined with an enzyme activity and enantio-selectivity which are as high as possible. As a rule, the temperature to be set is therefore dependent on the enzyme employed. The reaction temperature can be 10 to 100° C., preferably 15 to 60° C. and very preferably 20 to 45° C. The reaction temperature includes all values and subvalues therebetween, especially including 15, 20, 25, 30, 35, 40, 45, 50, 55, 60, 65, 70, 75, 80, 85, 90 and 95° C.

In the context of the present invention, the molecules at the beginning of the enzymatic reaction are called substrates, and the enzyme converts them into different molecules, the products.

The reaction according to the present invention can be carried out in substance, without a solvent, or in a solvent. There is no particular limitation on the type of solvent. Preferred are solvents that dissolve the substrates well. The reaction can be carried out in pure water. Since the substrates, however, are usually not very soluble in water, preferably aqueous or nonaqueous organic solvents are employed. Aqueous solvent mixtures include polar solvents such as alcohols, preferably lower alcohols. Organic solvents particularly preferably employed are those selected from the group consisting of esters, ethers, aromatic hydrocarbons, aliphatic hydrocarbons and halogenated hydrocarbons, and ketones, such as MEK (methyl-ethyl ketone) or MIBK (methyl-isobutyl ketone). The use of ethers, in particular methyl tert-butyl ether, as solvents is very particularly preferred.

An advantage of the reaction according to the present invention is the fact that the substrates can be employed in high initial and stationary concentrations. It has been shown by the inventors of the present invention that substrate concentrations of >50, preferably >100 and very particularly preferably >200 and extremely preferably of >300 g/l can be realized.

In the process according to the present invention, a procedure is preferably used where substrate(s) and enzyme are optionally initially introduced in a solvent. The resulting amine and the amide can be separated by means available to the person skilled in the art, preferably by means where in the final analysis both optical antipodes of the respective amine can be obtained in high enantiomeric enrichments after cleavage of the remaining amide. The reaction can also be carried out continuously, optionally in an enzyme-membrane reactor (J. Woltinger, A. Karau, W. Leuchtenberger, K. Drauz, Advances in Biochemical Engineering/Biotechnology 2005, 92 (Technology Transfer in Biotechnology), 289-316). In all cases, the enzyme employed can be recycled and employed again in the reaction. The carboxylic acid obtained after the cleavage of the amides can also be esterified again and employed in the reaction.

($C_1$-$C_8$)-Alkyl radicals are to be regarded as methyl, ethyl, n-propyl, isopropyl, n-butyl, isobutyl, sec-butyl, tert-butyl, pentyl, hexyl, heptyl or octyl, together with all their bond isomers.

The radical ($C_1$-$C_8$)-alkoxy corresponds to the radical ($C_1$-$C_8$)-alkyl above, with the proviso that this is bonded to the molecule via an oxygen atom.

As ($C_2$-$C_8$)-alkoxyalkyl, radicals are meant in which the alkyl chain is interrupted by at least one oxygen function, where two oxygen atoms cannot be bonded to one another. The number of the carbon atoms indicates the total number of the carbon atoms contained in the radical.

A ($C_2$-$C_8$)-alkylene bridge is a carbon chain having three to five C atoms, where this chain is bonded to the molecule considered via two different C atoms.

The radicals described in the preceding paragraphs can be mono- or polysubstituted by halogens and/or N, O, P, S, Si atom-containing radicals. These are in particular alkyl radicals of the abovementioned type, which contain one or more of these heteroatoms in their chain or which are bonded to the radical via one of these heteroatoms.

($C_3$-$C_8$)-Cycloalkyl is understood as meaning cyclopropyl, cyclobutyl, cyclopentyl, cyclohexyl or cycloheptyl radicals etc. These can be substituted by one or more halogens and/or N, O, P, S, Si atom-containing radicals and/or contain N, O, P, S atoms in the ring, such as, for example, 1-, 2-, 3-, 4-piperidyl, 1-, 2-, 3-pyrrolidinyl, 2-, 3-tetrahydrofuryl, 2-, 3-, 4-morpholinyl.

A ($C_3$-$C_8$)-cycloalkyl-($C_1$-$C_8$)-alkyl radical designates a cycloalkyl radical as shown above, which is bonded to the molecule via an alkyl radical as indicated above.

In the context of the present invention, ($C_1$-$C_8$)-acyloxy is an alkyl radical as defined above having at most 8 C atoms, which is bonded to the molecule via a COO— function.

In the context of the present invention, ($C_1$-$C_8$)-acyl is an alkyl radical as defined above having at most 8 C atoms, which is bonded to the molecule via a CO— function.

A ($C_6$-$C_{18}$)-aryl radical is understood as meaning an aromatic radical having 6 to 18 C atoms. In particular, these include compounds such as phenyl, naphthyl, anthryl, phenanthryl, biphenyl radicals or systems of the type previously described fused to the molecule concerned, such as, for example, indenyl systems, which can optionally be substituted by halogen, ($C_1$-$C_8$)-alkyl, ($C_1$-$C_8$)-alkoxy, $NH_2$, NH($C_1$-$C_8$)-alkyl, N(($C_1$-$C_8$)-alkyl)$_2$, OH, $CF_3$, NH($C_1$-$C_8$)-acyl, N(($C_1$-$C_8$)-acyl)$_2$, ($C_1$-$C_8$)-acyl, or ($C_1$-$C_8$)-acyloxy.

A ($C_7$-$C_{19}$)-aralkyl radical is a ($C_6$-$C_{18}$)-aryl radical bonded to the molecule via a ($C_1$-$C_8$)-alkyl radical.

In the context of the present invention, a ($C_3$-$C_{18}$)-heteroaryl radical designates a five-, six- or seven-membered aromatic ring system of 3 to 18 C atoms, which contains heteroatoms such as, for example, nitrogen, oxygen or sulphur in the ring. Such heteroaromatics are in particular regarded as radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical can be substituted by the same radicals as the abovementioned aryl radical.

A ($C_4$-$C_{19}$)-heteroaralkyl is understood as meaning a heteroaromatic system corresponding to the ($C_7$-$C_{19}$)-aralkyl radical.

Possible halogens (Hal) are fluorine, chlorine, bromine and iodine.

PEG is polyethylene glycol.

The term enantiomerically enriched or enantiomeric excess is understood in the context of the present invention as meaning the fraction of an enantiomer as a mixture with its optical antipodes in a range from >50% and <100%, preferably >90%. The ee value is calculated as follows:

([Enantiomer 1]−[enantiomer 2])/([enantiomer 1]+
[enantiomer 2])=ee value.

The ee value (enantiomeric excess) includes all values and subvalues therebetween, especially including 55, 60, 65, 70, 75, 80, 85, 90, 91, 92, 93, 94, 95, 96, 97, 98, 98.5, 99 and 99.5%.

Having generally described this invention, a further understanding can be obtained by reference to certain specific examples which are provided herein for purposes of illustration only, and are not intended to be limiting unless otherwise specified.

EXAMPLES

Example 1

Enzymatic Resolution of rac-1-phenylethyl-amine

A mixture of 1.446 g (1.2 mmol) of rac-1-phenylethyl-amine, 4.018 g (2.4 mmol) of ethyl methyl sulphonyl-acetate and 72.6 mg of lipase (immobilized lipase B from *Candida antarctica*, CALB, Novo 435) was prepared in 8.4 ml of methyl tert-butyl ether. Subsequently, the reaction mixture was stirred for 42 hours at a reaction temperature of 40° C. and then filtered off from the solid (immobilized lipase). The filtrate was subsequently freed from the solvent in vacuo. A $^1$H-NMR spectroscopic investigation of the crude product obtained showed a conversion of 52%. The determination of the enantiomeric excess showed an ee value of 99.1% for the remaining (S)-1-phenylethylamine, corresponding to an E value as a measure of the enantioselectivity of >100.

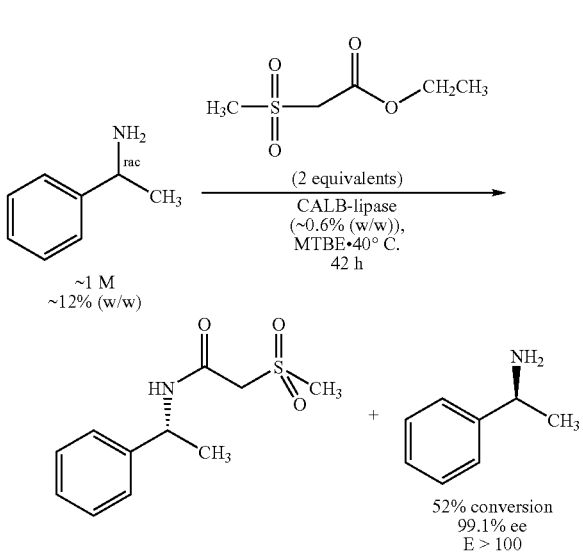

Example 2

Enzymatic Resolution of rac-1-(4-chloro-phenyl)ethylamine

A mixture of 1.60 g (1.03 mmol) of rac-1-(4-chlorophenyl)ethylamine, 3.39 g (2.04 mmol) of ethyl methylsulphonylacetate and 62 mg of lipase (immobilized lipase B from *Candida antarctica*, CALB, Novo 435) was prepared in 5.84 ml of methyl tert-butyl ether. Subsequently, the reaction mixture was stirred for 118 hours at a reaction temperature of 40-41° C. and then filtered off from the solid (immobilized lipase). The filtrate was subsequently freed from the solvent in vacuo. A $^1$H-NMR spectroscopic investigation of the crude product obtained showed a conversion of 48%. The determination of the enantiomeric excess showed an ee value of 87.7% for the remaining (S)-1-(4-chloro-phenyl)ethylamine, corresponding to an E value as a measure of the enantioselectivity of >100.

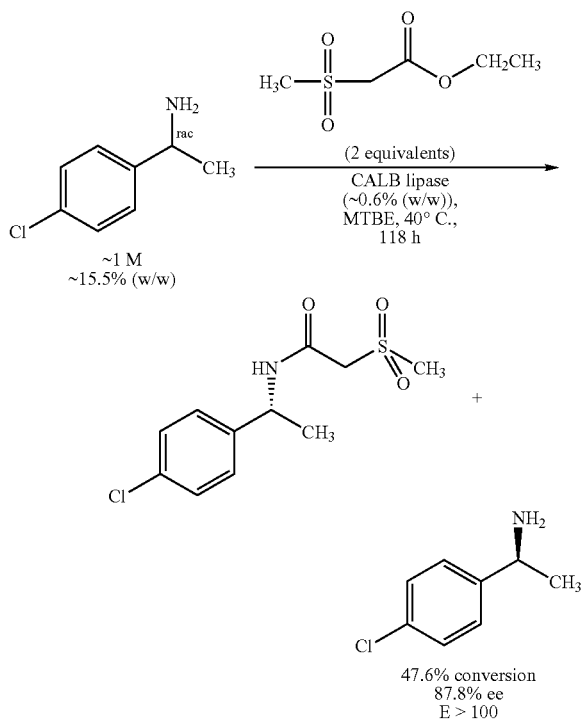

German patent application 102006028818.1 filed Jun. 21, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for the preparation of an enantiomerically enriched amine, comprising:

a) cleaving a racemic mixture of a reaction product of i) a chiral amine and ii) an acyl donor, in the presence of a hydrolase, to obtain a mixture of an enantiomerically enriched amide and an enantiomerically enriched amine; or b) reacting an amine with an acyl donor, in the presence of a hydrolase, to obtain a mixture of an enantiomerically enriched amide and an enantiomerically enriched amine; and c) separating the enantiomerically enriched amide from the enantiomerically enriched amine, wherein said acyl donor is a sulphonylacetic acid ester of the formula 2

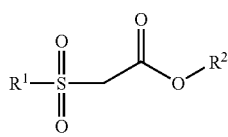

wherein $R^1$ and $R^2$ independently of one another are $(C_1\text{-}C_8)$-alkyl, HO—$(C_1\text{-}C_8)$-alkyl, $(C_2\text{-}C_8)$-alkoxyalkyl, $(C_6\text{-}C_{18})$-aryl, $(C_7\text{-}C_{19})$-aralkyl, $(C_3\text{-}C_{18})$-heteroaryl, $(C_4\text{-}C_{19})$-heteroaralkyl, $(C_1\text{-}C_8)$-alkyl-$(C_6\text{-}C_{19})$-aryl, $(C_1\text{-}C_8)$-alkyl-$(C_3\text{-}C_{18})$-heteroaryl, $(C_3\text{-}C_8)$-cyclo-alkyl, $(C_1\text{-}C_8)$-alkyl-$(C_3\text{-}C_8)$-cycloalkyl, or $(C_3\text{-}C_8)$-cycloalkyl-$(C_1\text{-}C_8)$-alkyl.

2. The process according to claim 1, wherein said sulphonylacetic acid ester is ethyl methylsulphonylacetate.

3. The process according to claim 1, wherein said hydrolase is a lipase from *Candida antarctica*.

4. The process according to claim 1, wherein a reaction temperature is 10 to 100° C.

5. The process according to claim 1, which is carried out in a solvent.

6. The process according to claim 1, which is carried out in methyl tert-butyl ether.

7. The process according to claim 1, wherein the substrate concentration is >100 g/l.

8. The process according to claim 1, wherein steps a) and c) are performed.

9. The process according to claim 1, wherein steps b) and c) are performed.

10. The process according to claim 1, wherein said hydrolase is a lipase from *Candida antarctica* in immobilized form.

11. The process according to claim 1, wherein a reaction temperature is 15 to 60° C.

12. The process according to claim 1, wherein a reaction temperature is 20 to 45° C.

13. The process according to claim 1, wherein said racemic mixture is rac-1-phenylethyl-amine.

14. The process according to claim 1, wherein said racemic mixture is rac-1-(4-chlorophenyl)ethylamine.

15. The process according to claim 1, wherein an enantiomeric excess of said enantiomerically enriched amine is >90%.

* * * * *